| United States Patent [19] | [11] Patent Number: 4,581,059 |
| Adams, Jr. et al. | [45] Date of Patent: Apr. 8, 1986 |

[54] HERBICIDAL PHENOXY ESTERS OF N-(HETEROCYCLIC)AMINOCARBONYL)-SULFAMIC ACID

[75] Inventors: John B. Adams, Jr.; Richard F. Sauers, both of Hockessin, Del.

[73] Assignee: E. I. Du Pont De Nemours and Company, Wilmington, Del.

[21] Appl. No.: 534,603

[22] Filed: Sep. 26, 1983

Related U.S. Application Data

[63] Continuation-in-part of Ser. No. 439,569, Nov. 5, 1982, abandoned.

[51] Int. Cl.$^4$ .................... C07D 239/47; A01N 47/36
[52] U.S. Cl. ........................................ 71/92; 544/211; 544/212; 544/321; 544/332; 71/93

[58] Field of Search ..................... 544/321, 332; 71/92

[56] References Cited

FOREIGN PATENT DOCUMENTS

| 3105453 | 10/1982 | Fed. Rep. of Germany | 544/332 |
| 3151450 | 7/1983 | Fed. Rep. of Germany | 71/90 |
| 3225471 | 1/1984 | Fed. Rep. of Germany | 544/332 |

*Primary Examiner*—Robert Gerstl

[57] ABSTRACT

Compounds of the class of phenoxy esters of N-[(heterocyclic)aminocarbonyl]sulfamic acid, such as N-[(4,6-dimethoxypyrimidin-2-yl)aminocarbonyl]sulfamic acid. 2-(trifluoromethylthio)phenyl ester, useful as pre-emergent or post-emergent herbicides.

15 Claims, No Drawings

HERBICIDAL PHENOXY ESTERS OF N-(HETEROCYCLIC)AMINOCARBONYL)SULFAMIC ACID

BACKGROUND OF THE INVENTION

This invention relates to novel phenoxy esters, such as N-[(4,6-dimethoxypyrimidin-2-yl)aminocarbonyl]sulfamic acid, 2-(trifluoromethylthio)phenyl ester, and their use in controlling undesired vegetation.

U.S. Pat. No. 4,191,553 discloses and claims N-(heterocyclicaminocarbonyl)arylsulfamates of the following general formula

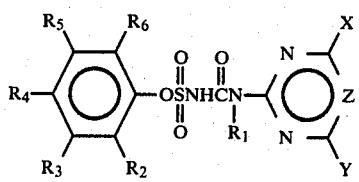

where
$R_1$ is H, $OCH_3$ or alkyl of 1–3 carbons;
$R_2$ is H, Cl, F, Br, $NO_2$, alkyl of 1–4 carbons, alkoxy of 1–4 carbons, $CF_3$ or

$-CR_7$;

$R_3$ is H, Cl, F, Br, $CH_3$ or alkoxy of 1–4 carbons;
$R_4$ is H, Cl, F, Br, $NO_2$, alkyl of 1–4 carbons, alkoxy of 1–4 carbons, CN or

$-CR_7$;

$R_5$ is H, Cl, F, Br, $CH_3$, $NO_2$ or $CF_3$;
$R_6$ is H, Cl, F, Br, alkyl of 1–4 carbons or alkoxy of 1–4 carbons;
$R_7$ is Na—O—, OH or alkoxy of 1–4 carbons; X is $CH_3$, $CH_3CH_2$, alkoxy of 1–3 carbons, $CH_3OCH_2$, $CH_3OCH_2CH_2O$, $CH_3S$, $CH_3CH_2S$, $CF_3$ or Cl;
Y is $CH_3$, $CH_3CH_2$, alkoxy of 1–3 carbons, $CH_3OCH_2$, $CH_3OCH_2CH_2O$, $CH_3S$ or $CH_3CH_2S$; and
Z is CH or N.

These compounds are described as general and selective pre- and post-emergence herbicides and as plant growth regulants.

U.S. patent application Ser. No. 152021 now U.S. Pat. No. 4,452,628, issued June 5, 1984, discloses and claims herbicidally effective compounds of the general formula

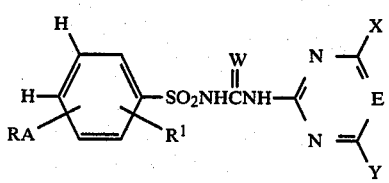

wherein W can be O or S;
R can be $CF_3$;
A can be $S(O)_n$, where n is 0, 1 or 2;
$R^1$ can be H, F, Cl, Br or $CH_3$;
E can be CH or N; and
X and Y can be $CH_3$ or $OCH_3$.

It is taught that these compounds can be applied either pre- or post-emergence for the control of undesired vegetation in non-crop areas or for selective weed control in certain crops, such as wheat.

South African Pat. No. 814874 discloses N-phenylsulfonyl-N'-pyrimidinyl- and triazinylureas of the formula

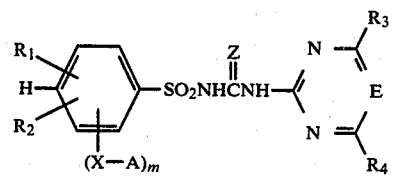

wherein X can be a sulfinyl or sulfonyl bridge;
A can be an alkyl radical which is substituted by halogen;
E can be CH or N;
Z can be O or S;
$R_1$ and $R_2$ can be H; and
$R_3$ and $R_4$ can be H or alkyl,
among other values.

U.S. Pat. No. 4,394,153, issued July 19, 1983 to Reap discloses herbicidal sulfamoylureas incorporating an ortho sulfonate ester or amide.

SUMMARY OF THE INVENTION

This invention relates to novel compounds of Formula I, to suitable agricultural compositions containing them as an active ingredient, and to their method-of-use as pre-emergent or post-emergent herbicides or plant growth regulants.

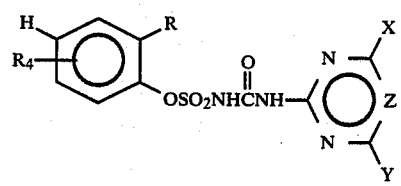

wherein
R is $QR_1$, $SO_2NR_2R_3$ or $OSO_2NR_2R_3$;
$R_1$ is $C_1$–$C_3$ alkyl, $CH_2CH=CH_2$, $CF_3$, $CF_2H$ or $CF_2CF_2H$;
$R_2$ and $R_3$ are independently $C_1$–$C_3$ alkyl;
$R_4$ is H, $CH_3$, $OCH_3$, Cl, $NO_2$, F or $CF_3$;
Q is O, S, S(O) or $SO_2$;
X is $CH_3$ or $OCH_3$;
Y is $CH_3$, $OCH_3$, $C_2H_5$, $OC_2H_5$, $CH_2OCH_3$, $CH(OCH_3)_2$, Cl, Br or

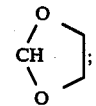

and
Z is CH or N;
and their agriculturally suitable salts provided that:
(1) the total number of carbon atoms of $R_2$ and $R_3$ is less than or equal to 4;

(2) when Y is Cl or Br, then Z is CH and X is $OCH_3$; and (3) when Q is O, then $R_1$ is $CF_3$, $CF_2H$ or $CF_2CF_2H$.

Preferred for reasons of their higher herbicidal activity, greater plant-growth-regulant activity and/or more favorable ease of synthesis are:

(1) Compounds of Formula I where R is $QR_1$ or $SO_2NR_2R_3$; Q is O, S or $SO_2$; $R_1$ is $C_1$-$C_3$ alkyl, $CH_2CH=CH_2$, $CF_3$ or $CF_2H$; and $R_4$ is H.

(2) Compounds of Preferred (1) where $R_1$ is $CH_3$, $CF_3$ or $CF_2H$; $R_2$ and $R_3$ are $CH_3$; and Q is O or S.

Specifically preferred for reasons of their highest herbicidal activity, greatest plant-growth-regulant activity and/or most favorable ease of synthesis are:

N-[(4,6-dimethoxypyrimidin-2-yl)aminocarbonyl]sulfamic acid, 2-(trifluoromethylthio)phenyl ester; and N-[(4,6-dimethoxypyrimidin-2-yl)aminocarbonyl]sulfamic acid, 2-(difluoromethylthio)phenyl ester.

DETAILED DESCRIPTION OF THE INVENTION

Synthesis

The compounds of Formula I, where R is other than $S(O)R_1$, can be prepared, as shown in Scheme I, by reacting an appropriate 2-aminopyrimidine or 2-aminotriazine of Formula II with an appropriately substituted aryloxysulfonyl isocyanate of Formula III.

Scheme I

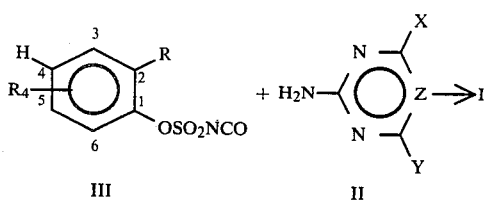

The reaction is best carried out in an inert organic solvent such as methylene chloride or acetonitrile. The mode of addition is not critical, however, it is often convenient to add a solution of the isocyanate III to a stirred suspension of the aminoheterocycle II.

The reaction is generally exothermic. In some cases, the compounds of Formula I are insoluble in the reaction solvent and crystallize from it in pure form. Products which are soluble in the reaction solvent can be isolated by evaporation of the solvent and trituration of the residue with solvents such as ethyl ether, 1-chlorobutane, hexane or ethanol.

The sulfoxides of Formula IV, of this invention, can be prepared by oxidation of sulfides of Formula V as shown in Scheme II.

Scheme II

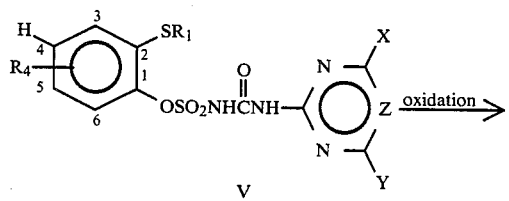

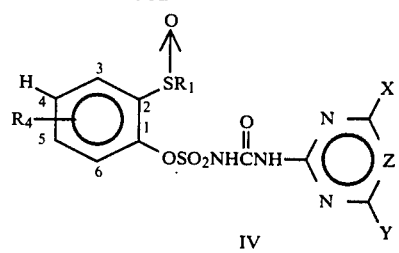

The sulfoxides of Formula IV can be prepared by oxidation of sulfides V by treatment with one molar equivalent of m-chloroperoxybenzoic acid in a halogenated hydrocarbon solvent such as methylene chloride or chloroform.

Alternatively, sulfoxides of Formula IV can be prepared by oxidation of sulfides V by treatment with one molar equivalent of hydrogen peroxide in acetic acid.

The intermediate aryloxysulfonyl isocyanates of Formula III, where R is other than $S(O)R_1$, can be prepared according to the procedure of Lohaus, Chem. Ber., 105, 2791 (1972), by reacting a substituted phenol of Formula VI, where R is other than $S(O)R_1$, with chlorosulfonyl isocyanate and heating to reflux in solvents such as chlorobenzene or xylene (Scheme III).

Scheme III

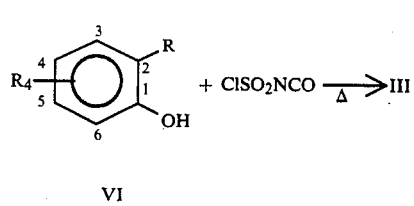

Phenols of Formula VI, where R is other than $SOR_1$, $OCF_3$, $OCF_2H$ or $OCF_2CF_2H$ can be prepared from the corresponding aniline by hydrolysis of benzenediazonium salts as described in "Survey of Organic Syntheses", C. A. Buehler and D. E. Pearson, Wiley Interscience Publishers, pp 255-257, and references cited therein.

In addition, phenols of Formula VI where R is $SR_1$ and $R_1$ is other than $CF_3$, $CF_2H$ or $CF_2CF_2H$ can be prepared by alkylation of commercially available o-mercaptophenol as described in Tetrahedron 26, 4449 (1970).

Phenols of Formula VI where R is $OCF_3$, $OCF_2H$ or $OCF_2CF_2H$ can be prepared by the method shown in Scheme IV. Alkylation of the commercially available o-benzyloxyphenol VII with tetrafluoroethylene, chlorodifluoromethane or chlorotrifluoromethane gives the respective bis-ether of Formula VIII, where $R_5$ is $CF_3$, $CF_2H$ or $CF_2CF_2H$. Hydrogenolysis of compounds of Formula VIII gives phenols of Formula IX where $R_5$ is $CF_3$, $CF_2H$ or $CF_2CF_2H$.

Scheme IV

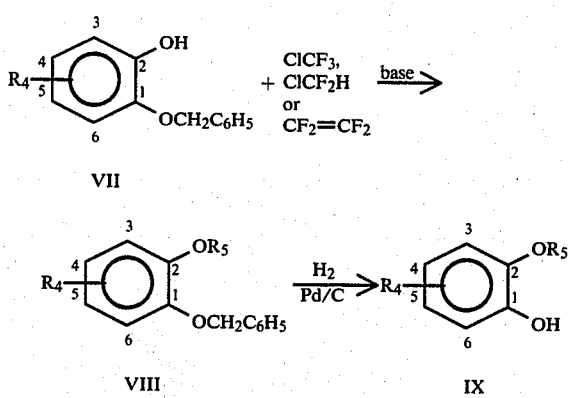

The synthesis of the heterocyclic amines of Formula II has been reviewed in "The Chemistry of Heterocyclic Compounds", a series published by Interscience Publishers. 2-Aminopyrimidines are described by D. J. Brown in "The Pyrimidines" in Vol. XVI of the series; 2-aminotriazines are described by E. M. Smolin and L. Rapoport in "s-Triazines and Derivatives", in Vol. XIII of the series, both of the teachings of which are herein incorporated by reference.

The compounds of this invention are further illustrated by the following examples, wherein temperatures are given in degrees centigrade and parts are by weight unless otherwise indicated.

EXAMPLE 1

2-(Trifluoromethylthio)phenol

A. Concentrated sulfuric acid (22.1 g) was added at ~15° to a solution of 18.4 g of 2-(trifluoromethylthio)-benzenamine in 80 ml of acetic acid. To the resulting white suspension, 7.8 g of sodium nitrite was added portionwise over 10-15 minutes at 10°-15°. When addition of sodium nitrite was complete, 25 ml of acetic acid was added and the resulting yellow suspension stirred 15 minutes.

B. A mixture of 90 ml of concentrated sulfuric acid and 150 ml water was heated to 125°-135°. To the sulfuric acid solution, the diazonium sulfate prepared in Part A was added dropwise over 15-30 minutes during simultaneous steam distillation. The aqueous distillate was extracted with methylene chloride. The organic solution was washed with water, dried over anhydrous magnesium sulfate and decolorized with charcoal. The organic solution was filtered and the solvent evaporated under reduced pressure to give 16.0 g of the crude phenol.

EXAMPLE 2

2-(Trifluoromethylthio)phenoxysulfonyl isocyanate

A solution of 15.0 g of 2-(trifluoromethylthio)phenol in 100 ml of chlorobenzene was cooled to 0° and 11.2 g of chlorosulfonyl isocyanate was added dropwise. The resulting solution was allowed to warm to room temperature, then heated at reflux for 2.25 hours. The reaction solution was cooled and the solvent evaporated under reduced pressure. Distillation of the residual oil gave 12.6 g of the title sulfonyl isocyanate as a yellowish liquid bp 85°-92° (0.5-3.0 mm).

EXAMPLE 3

N-[4,6-Dimethoxypyrimidin-2-yl)aminocarbonyl]sulfamic acid, 2-(trifluoromethylthio)phenyl ester To a solution of 0.7 g of 2-amino-4,6-dimethoxypyrimidine in 10 ml of methylene chloride was added 1.5 g of 2-(trifluoromethylthio)phenoxysulfonyl isocyanate. The reaction solution exotherms mildly and is then stirred at ambient temperature for 3 hours. The solvent was evaporated at reduced pressure. Trituration of the residual solid with 1-chlorobutane gave 1.4 g of light yellow solid, m.p. 128°-130°.

EXAMPLE 4

1-(Phenylmethoxy)-2-(1,1,2,2-tetrafluoroethoxy)benzene

A Hastelloy pressure vessel was charged with 50 g of o-(benzyloxy)phenol, 2.3 g of potassium hydroxide, and 79 ml of N,N-dimethylformamide. The vessel was evacuated, and then charged with 26 g of tetrafluoroethylene. The vessel was sealed and heated at 85° internal temperature for 4 hours, and then cooled, vented and the contents poured into ice water. The resulting aqueous mixture was extracted with 1-chlorobutane. The organic solution was washed successively with 1N sodium hydroxide solution, twice with water, and saturated brine. The organic solution was then dried over anhydrous magnesium sulfate, filtered and the solvent evaporated under reduced pressure to yield a residual orange oil, which was distilled, giving 60.65 g of the title compound as a colorless oil, bp 120°-130° (0.2 mm).

EXAMPLE 5

2-(1,1,2,2-Tetrafluoroethoxy)phenol

A solution of 58.6 g of 1-(phenylmethoxy)-2-(1,1,2,2-tetrafluoroethoxy)benzene in 200 ml methanol was blanketed with nitrogen and 1.0 g of 10% palladium on charcoal added. The mixture was hydrogenated at 50 psi hydrogen for 3 hours. The reaction mixture was filtered to remove catalyst and the filtrate concentrated under reduced pressure to give an oil, which darkened on standing. The oil was distilled, bp 25°-32° (0.2 mm), to give the phenol as a colorless oil, which solidified on standing. The infrared spectrum showed OH absorption at 3570 cm$^{-1}$.

EXAMPLE 6

2-(1,1,2,2-Tetrafluoroethoxy)phenoxysulfonyl isocyanate

Chlorosulfonyl isocyanate (4.4 ml) was added to a cooled solution of 10.5 g of 2-(1,1,2,2-tetrafluoroethoxy)phenol in 50 ml chlorobenzene. The reaction solution was heated at reflux for 2.3 hours, then cooled and the solvent evaporated under reduced pressure, giving the sulfonyl isocyanate as an oil. The infrared spectrum showed NCO absorption at 2255 cm$^{-1}$. The crude sulfonyl isocyanate was dissolved in and then diluted with acetonitrile to a volume of 50 ml, giving an approximately 1 molar solution of the isocyanate.

EXAMPLE 7

N-[(4,6-Dimethoxy-1,3,5-triazin-2-yl)aminosulfonyl]-sulfamic acid, 2-(1,1,2,2-tetrafluoroethoxy)phenylester To 0.78 g of 2-amino-4,6-dimethoxy-1,3,5-triazine was added 5 ml of the 1M acetonitile solution of the sulfonyl isocyanate prepared in Example 6. Dissolution of the aminotriazine occurred and the mixture was stirred overnight. The resulting suspension was filtered and the solid rinsed with acetonitrile to give 0.53 g of white solid, m.p. 157°–162° (dec).

Mass-spectral analysis showed a characteristic fragment pattern for the title compound

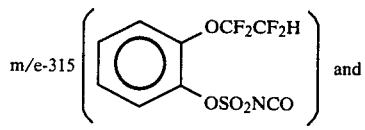

and

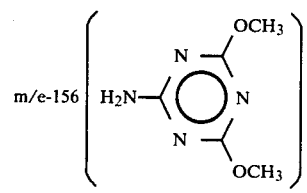

EXAMPLE 8

2-(Dimethylaminosulfamoyl)phenoxysulfonyl isocyanate

To 5.2 ml (0.06 mole) chlorosulfonyl isocyanate in 75 ml dry xylenes was added 10.1 g (0.05 mole) of 2-(dimethylaminosulfamoyl)phenol in 15 ml xylenes, keeping the reaction temperature <5° C. This mixture was then heated to reflux temperature for 1 hour. The reaction solution was then cooled and the solvent evaporated to give an oil. The infrared spectrum showed NCO absorption at 2270 cm$^{-1}$.

EXAMPLE 9

N-[(4,6-Dimethoxypyrimidin-2-yl)aminocarbonyl]sulfamic acid, 2-(dimethylaminosulfamoyl)phenyl ester To a solution of 0.54 g 2-amino-4,6-dimethoxypyrimidine in 10 ml methylene chloride was added 1.6 g of 2-(dimethylaminosulfamoyl)phenoxysulfonyl isocyanate. The reaction exothermed (23°–32° C.) and was stirred at room temperature for 2 hours. The solvent was evaporated at reduced pressure. The resultant orange oil was triturated with ethanol and white solids filtered to give 0.6 g, m.p. 115°–117° C.

Mass-spectral analysis showed a characteristic fragment pattern for the title compound.

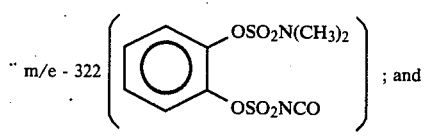

; and

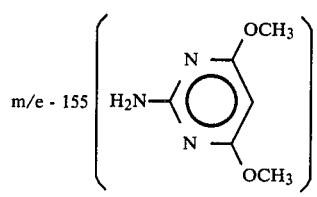

By the procedures of Examples 1–9, the following compounds can be prepared. Tables I and II are meant to be illustrative of the breadth of this invention and are not meant to be all-inclusive.

TABLE I

| R | X | Y | R$_4$ | m.p. (°C.) |
|---|---|---|---|---|
| SCF$_3$ | CH$_3$ | OCH$_3$ | H | 136–139° |
| SCF$_3$ | OCH$_3$ | OCH$_3$ | H | 128–130° |
| SCF$_3$ | CH$_3$ | CH$_3$ | H | 126–129° |
| SCF$_3$ | OCH$_3$ | OC$_2$H$_5$ | H | |
| SCF$_3$ | OCH$_3$ | Cl | H | 145–146.5° |
| SCF$_3$ | CH$_3$ | CH(OCH$_3$)$_2$ | H | |
| SCF$_3$ | OCH$_3$ | HC(O-CH$_2$-CH$_2$-O) | H | |
| SCF$_3$ | OCH$_3$ | CH$_2$OCH$_3$ | H | |
| SCF$_3$ | OCH$_3$ | C$_2$H$_5$ | H | |
| SOCF$_3$ | CH$_3$ | OCH$_3$ | H | |
| SOCF$_3$ | OCH$_3$ | OCH$_3$ | H | |
| SOCF$_3$ | OCH$_3$ | Cl | H | |
| SOCF$_3$ | CH$_3$ | OC$_2$H$_5$ | H | |
| SO$_2$CF$_3$ | OCH$_3$ | OCH$_3$ | H | 82–86°(d) |
| SO$_2$CF$_3$ | CH$_3$ | CH$_3$ | H | 122–124° |
| SO$_2$CF$_3$ | CH$_3$ | OCH$_3$ | H | 89–95° |
| SO$_2$CF$_3$ | OCH$_3$ | Cl | H | |
| SCF$_2$H | OCH$_3$ | OCH$_3$ | H | |
| SCF$_2$H | CH$_3$ | OCH$_3$ | H | |
| SCF$_2$H | CH$_3$ | CH$_3$ | H | |
| SOCF$_2$H | CH$_3$ | CH$_3$ | H | |
| SOCF$_2$H | OCH$_3$ | OCH$_3$ | H | |
| SOCF$_2$H | CH$_3$ | OCH$_3$ | H | |
| SO$_2$CF$_2$H | CH$_3$ | CH$_3$ | H | |
| SO$_2$CF$_2$H | OCH$_3$ | OCH$_3$ | H | |
| SO$_2$CF$_2$H | CH$_3$ | OCH$_3$ | H | |
| SCF$_2$CF$_2$H | CH$_3$ | OCH$_3$ | H | |
| SCF$_2$CF$_2$H | OCH$_3$ | OCH$_3$ | H | |
| SCF$_2$CF$_2$H | CH$_3$ | CH$_3$ | H | |
| SOCF$_2$CF$_2$H | CH$_3$ | CH$_3$ | H | |
| SO$_2$CF$_2$CF$_2$H | OCH$_3$ | OCH$_3$ | H | |
| SCH$_3$ | CH$_3$ | CH$_3$ | H | 83–119 |
| SCH$_3$ | OCH$_3$ | OCH$_3$ | H | 151–158 |
| SCH$_3$ | CH$_3$ | OCH$_3$ | H | 90–125 |
| SOCH$_3$ | CH$_3$ | CH$_3$ | H | |
| SOCH$_3$ | OCH$_3$ | OCH$_3$ | H | |
| SOCH$_3$ | CH$_3$ | OCH$_3$ | H | |
| SO$_2$CH$_3$ | CH$_3$ | CH$_3$ | H | |
| SO$_2$CH$_3$ | OCH$_3$ | OCH$_3$ | H | |
| SO$_2$CH$_3$ | CH$_3$ | OCH$_3$ | H | |
| SOC$_2$H$_5$ | CH$_3$ | OCH$_3$ | H | |
| SO$_2$C$_2$H$_5$ | OCH$_3$ | OCH$_3$ | H | |
| SO$_2$C$_3$H$_7$ | CH$_3$ | OCH$_3$ | H | |
| SO$_2$C$_3$H$_7$ | OCH$_3$ | OCH$_3$ | H | |
| SO$_2$N(CH$_3$)$_2$ | CH$_3$ | CH$_3$ | H | 107–123 |
| SO$_2$N(CH$_3$)$_2$ | OCH$_3$ | OCH$_3$ | H | 117–131 |
| SO$_2$N(CH$_3$)$_2$ | OCH$_3$ | OCH$_3$ | H | 104–131 |
| SO$_2$N(CH$_3$)C$_2$H$_5$ | CH$_3$ | CH$_3$ | H | |
| SO$_2$N(CH$_3$)C$_2$H$_5$ | OCH$_3$ | CH$_3$ | H | |
| SO$_2$N(CH$_3$)C$_2$H$_5$ | OCH$_3$ | OCH$_3$ | H | |
| SO$_2$N(CH$_3$)C$_3$H$_7$ | CH$_3$ | OCH$_3$ | H | |
| SO$_2$N(CH$_3$)C$_3$H$_7$ | CH$_3$ | CH$_3$ | H | |
| SO$_2$N(CH$_3$)C$_3$H$_7$ | OCH$_3$ | OCH$_3$ | H | |
| OCF$_2$CF$_2$H | CH$_3$ | CH$_3$ | H | gum |
| OCF$_2$CF$_2$H | OCH$_3$ | CH$_3$ | H | gum |
| OCF$_2$CF$_2$H | OCH$_3$ | OCH$_3$ | H | 136–139° |
| OCF$_2$CF$_2$H | OCH$_3$ | Cl | H | 115–118° |
| OCF$_3$ | OCH$_3$ | OCH$_3$ | H | |
| OCF$_3$ | CH$_3$ | OCH$_3$ | H | |
| OCF$_3$ | CH$_3$ | CH$_3$ | H | |
| OCF$_2$H | CH$_3$ | CH$_3$ | H | |
| OCF$_2$H | CH$_3$ | OCH$_3$ | H | |

TABLE I-continued

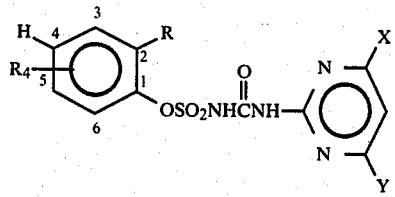

| R | X | Y | R4 | m.p. (°C.) |
|---|---|---|----|-----------|
| OCF2H | OCH3 | OCH3 | H | |
| OCF2H | OCH3 | CH(OCH3)2 | H | |
| OSO2N(CH3)2 | OCH3 | OCH3 | H | 115–117 |
| OSO2N(CH3)2 | OCH3 | CH3 | H | oil |
| OSO2N(CH3)2 | CH3 | CH3 | H | oil |
| SCH2CH=CH2 | OCH3 | OCH3 | H | |
| SCH2CH=CH2 | OCH3 | CH3 | H | |
| SCH2CH=CH2 | CH3 | CH3 | H | |
| OSO2N(CH3)C2H5 | OCH3 | OCH3 | H | |
| OSO2N(CH3)C2H5 | OCH3 | CH3 | H | |
| OSO2N(CH3)C2H5 | CH3 | CH3 | H | |
| OSO2N(CH3)C3H7 | OCH3 | OCH3 | H | |
| OSO2N(CH3)2 | CH3 | OCH2CH3 | H | |
| SCH3 | OCH3 | C2H5 | H | |
| OSO2N(CH3)2 | OCH3 | C2H5 | H | |
| SCH3 | OCH3 | CH2OCH3 | H | |
| SCH3 | CH3 | CH(OCH3)2 | H | |
| SCH3 | OCH3 | CH(OCH3)2 | H | |
| SO2N(CH3)2 | OCH3 | CH(OCH3)2 | H | |
| SO2N(CH3)2 | CH3 | CH(OCH3)2 | H | |
| SO2N(CH3)2 | OCH3 | Cl | H | |
| SO2N(CH3)2 | OCH3 | Br | H | |
| SCH3 | OCH3 | Br | H | |
| SO2N(CH3)2 | OCH3 | [dioxolane] | H | |
| SO2N(CH3)2 | CH3 | [dioxolane] | H | |
| SCH3 | OCH3 | OCH3 | 3-CH3 | |
| SCH3 | OCH3 | CH3 | 3-CH3 | |
| SCH3 | CH3 | CH3 | 3-CH3 | |
| SCH3 | OCH3 | OCH3 | 5-Cl | |
| SCH3 | OCH3 | CH3 | 5-Cl | |
| SCH3 | CH3 | CH3 | 5-Cl | |
| SCH3 | OCH3 | OCH3 | 5-OCH3 | |
| SCH3 | OCH3 | CH3 | 5-OCH3 | |
| SCH3 | CH3 | CH3 | 5-OCH3 | |
| SCH3 | OCH3 | OCH3 | 5-CF3 | |
| SCH3 | OCH3 | CH3 | 5-CF3 | |
| SCH3 | CH3 | CH3 | 5-CF3 | |
| SCH3 | OCH3 | OCH3 | 5-NO2 | |
| SCH3 | OCH3 | CH3 | 5-NO2 | |
| SCH3 | CH3 | CH3 | 5-NO2 | |
| SCH3 | OCH3 | OCH3 | 5-F | |
| SCH3 | OCH3 | OCH3 | 6-CH3 | |
| SCH3 | OCH3 | CH3 | 6-CH3 | |
| SCH3 | CH3 | CH3 | 6-CH3 | |

TABLE II

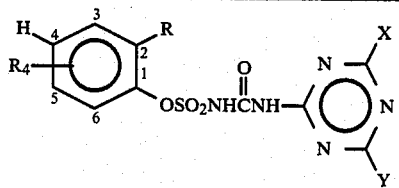

| R | X | Y | R4 | m.p. (°C.) |
|---|---|---|----|-----------|
| SCF3 | CH3 | OCH3 | H | 87–89° |

TABLE II-continued

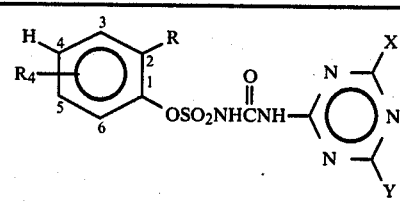

| R | X | Y | R4 | m.p. (°C.) |
|---|---|---|----|-----------|
| SCF3 | OCH3 | OCH3 | H | |
| SCF3 | CH3 | CH3 | H | |
| SCF3 | OCH3 | OC2H5 | H | |
| SCF3 | CH3 | CH(OCH3)2 | H | |
| SCF3 | OCH3 | [dioxolane] | H | |
| SCF3 | OCH3 | CH2OCH3 | H | |
| SCF3 | OCH3 | C2H5 | H | |
| SOCF3 | CH3 | OCH3 | H | |
| SOCF3 | OCH3 | OCH3 | H | |
| SOCF3 | CH3 | OC2H5 | H | |
| SO2CF3 | OCH3 | OCH3 | H | gum |
| SO2CF3 | CH3 | CH3 | H | 122–124° |
| SO2CF3 | CH3 | OCH3 | H | 111–114° |
| SCF2H | OCH3 | OCH3 | H | |
| SCF2H | CH3 | CH3 | H | |
| SOCF2H | CH3 | CH3 | H | |
| SOCF2H | OCH3 | OCH3 | H | |
| SO2CF2H | CH3 | CH3 | H | |
| SO2CF2H | OCH3 | OCH3 | H | |
| SCF2CF2H | CH3 | OCH3 | H | |
| SCF2CF2H | OCH3 | OCH3 | H | |
| SCF2CF2H | CH3 | OCH3 | H | |
| SOCF2CF2H | OCH3 | OCH3 | H | |
| SO2CF2CF2H | OCH3 | OCH3 | H | |
| SCH3 | CH3 | CH3 | H | |
| SCH3 | OCH3 | OCH3 | H | 204 |
| SCH3 | CH3 | OCH3 | H | 87–163 |
| SOCH3 | CH3 | CH3 | H | |
| SOCH3 | OCH3 | OCH3 | H | |
| SOCH3 | CH3 | OCH3 | H | |
| SO2CH3 | CH3 | CH3 | H | |
| SO2CH3 | OCH3 | OCH3 | H | |
| SO2CH3 | CH3 | OCH3 | H | |
| SOC2H5 | CH3 | CH3 | H | |
| SO2C2H5 | OCH3 | OCH3 | H | |
| SO2C3H7 | CH3 | CH3 | H | |
| SO2C3H7 | OCH3 | OCH3 | H | |
| SO2N(CH3)2 | CH3 | CH3 | H | |
| SO2N(CH3)2 | OCH3 | OCH3 | H | oil |
| SO2N(CH3)2 | CH3 | OCH3 | H | 88–119 |
| SO2N(CH3)C2H5 | CH3 | CH3 | H | |
| SO2N(CH3)C2H5 | OCH3 | CH3 | H | |
| SO2N(CH3)C2H5 | OCH3 | OCH3 | H | |
| SO2N(CH3)C3H7 | OCH3 | CH3 | H | |
| SO2N(CH3)C3H7 | CH3 | CH3 | H | |
| SO2N(CH3)C3H7 | OCH3 | OCH3 | H | |
| OCF2CF2H | CH3 | CH3 | H | 97–115° |
| OCF2CF2H | OCH3 | CH3 | H | 139–140° |
| OCF2CF2H | OCH3 | OCH3 | H | 157–162°(d) |
| OCF3 | OCH3 | OCH3 | H | |
| OCF3 | OCH3 | CH3 | H | |
| OCF3 | CH3 | CH3 | H | |
| OCF2H | CH3 | CH3 | H | |
| OCF2H | CH3 | OCH3 | H | |
| OCF2H | OCH3 | OCH3 | H | |
| OCF2H | OCH3 | CH(OCH3)2 | H | |
| OSO2N(CH3)2 | OCH3 | CH3 | H | 126–128.5 |
| OSO2N(CH3)2 | OCH3 | OCH3 | H | 142–147 |
| OCH2CH=CH2 | OCH3 | OCH3 | H | |
| SCH2CH=CH2 | OCH3 | OCH3 | H | |
| OSO2N(CH3)C2H5 | OCH3 | OCH3 | H | |
| OSO2N(CH3)C2H5 | OCH3 | CH3 | H | |

TABLE II-continued $$\underset{R_4}{\overset{H}{\underset{5}{\bigcirc}}}\underset{6}{\overset{3}{\underset{2}{\bigcirc}}}\underset{1}{\overset{R}{\underset{OSO_2NHCNH}{\bigcirc}}}\underset{N}{\overset{X}{\underset{Y}{\bigcirc}}}$$

| R | X | Y | $R_4$ | m.p. (°C.) |
|---|---|---|---|---|
| $OSO_2N(CH_3)C_3H_7$ | $OCH_3$ | $OCH_3$ | H | |
| $SCH_3$ | $OCH_3$ | $OCH_3$ | 3-$CH_3$ | |
| $SCH_3$ | $OCH_3$ | $OCH_3$ | 6-$CH_3$ | |
| $SCH_3$ | $OCH_3$ | $OCH_3$ | 5-Cl | |
| $SCH_3$ | $OCH_3$ | $OCH_3$ | 5-F | |
| $SCH_3$ | $OCH_3$ | $OCH_3$ | 5-$CF_3$ | |
| $SCH_3$ | $OCH_3$ | $OCH_3$ | 5-$NO_2$ | |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High-strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE III

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High-Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer- or fluid-energy mill. Suspensions are prepared by wet milling (see, for example, Littler, U.S. Pat. No. 3,060,084). Granules and pellets may be made by spraying the active material upon preformed granular carriers or by agglomeration techniques as may be seen in J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. w. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weel Control Handbook", 5th Ed., Blackwell Scientific Publications, Oxford, 1968, pp. 101–103.

In the following examples, all parts are by weight unless otherwise indicated.

EXAMPLE 10

Wettable Powder

| | |
|---|---|
| N—[(4,6-dimethoxypyrimidin-2-yl)amino-carbonyl]sulfamic acid, 2-(trifluoromethylthio)phenyl ester | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are substantially under 50 microns, reblended, and packaged.

EXAMPLE 11

Wettable Powder

| | |
|---|---|
| N—[(4,6-dimethoxypyrimidin-2-yl)amino-carbonyl]sulfamic acid, 2-(difluoromethylthio)phenyl ester | 50% |
| sodium alkylnaphthalenesulfonate | 2% |
| low-viscosity methyl cellulose | 2% |
| diatomaceous earth | 46% |

The ingredients are blended, coarsely hammer-milled and then air-milled to produce particles substantially all below 10 microns in diameter. The product is reblended before packaging.

EXAMPLE 12

Granule

| | |
|---|---|
| Wettable Powder of Example 11 | 5% |
| attapulgite granules (U.S.S. 20–40 mesh; 0.84–0.42 mm) | 95% |

A slurry of wettable powder containing ≈25% solids is sprayed on the surface of attapulgite granules while tumbling in a double-cone blender. The granules are dried and packaged.

EXAMPLE 13

Extruded Pellet

| | |
|---|---|
| N—[(4,6-dimethoxypyrimidin-2-yl)amino-carbonyl]sulfamic acid, 2-(trifluoromethylthio)phenyl ester | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These can be used directly after drying, or the dried pellets can be crushed to pass a U.S. Ser. No. 20 sieve (0.84 mm openings). The granules held on a U.S. Ser. No. 40 sieve (0.42 mm openings) can be packaged for use and the fines recycled.

EXAMPLE 14

Oil Suspension

| | |
|---|---|
| N—[(4,6-dimethoxypyrimidin-2-yl)amino-carbonyl]sulfamic acid, 2-(trifluoromethylthio)phenyl ester | 25% |
| polyoxyethylene sorbitol hexaoleate | 5% |
| highly-aliphatic hydrocarbon oil | 70% |

The ingredients are ground together in a sand mill until the solid particles have been reduced to under about 5 microns. The resulting thick suspension can be applied directly, but preferably after being extended with oils or emulsified in water.

EXAMPLE 15

Wettable Powder

| | |
|---|---|
| N—[(4,6-dimethoxypyrimidin-2-yl)amino-carbonyl]sulfamic acid, 2-(trifluoromethylthio)phenyl ester | 20% |
| sodium alkylnaphthalenesulfonate | 4% |
| sodium ligninsulfonate | 4% |
| low-viscosity methyl cellulose | 3% |
| attapulgite | 69% |

The ingredients are thoroughly blended. After grinding in a hammer-mill to produce particles substantially all below 100 microns, the material is reblended and sifted through a U.S. Ser. No. 50 sieve (0.3 mm opening) and packaged.

EXAMPLE 16

Low Strength Granule

| | |
|---|---|
| N—[(4,6-dimethoxypyrimidin-2-yl)amino-carbonyl]sulfamic acid, 2-(trifluoromethylthio)phenyl ester | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double-cone blender. After spraying of the solution has been completed, the blender is allowed to run for a short period and then the granules are packaged.

EXAMPLE 17

Aqueous Suspension

| | |
|---|---|
| N—[(4,6-dimethoxyprimidin-2-yl)amino-carbonyl]sulfamic acid, 2-(trifluoromethylthio)phenyl ester | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles substantially all under 5 microns in size.

EXAMPLE 18

Solution

| | |
|---|---|
| N—[(4,6-dimethoxypyrimidin-2-yl)amino-carbonyl]sulfamic acid, 2-(difluoromethylthio)phenyl ester, sodium salt | 5% |
| water | 95% |

The salt is added directly to the water with stirring to produce the solution, which can then be packaged for use.

EXAMPLE 19

Low Strength Granule

| | |
|---|---|
| N—[(4,6-dimethoxypyrimidin-2-yl)amino-carbonyl]sulfamic acid, 2-(difluoromethylthio)phenyl ester | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 20

Granule

| | |
|---|---|
| N—[(4,6-dimethoxypyrimidin-2-yl)amino- | 80% |

| | |
|---|---|
| carbonyl]sulfamic acid, 2-(trifluoromethylthio)phenyl ester wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid-bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 21

High Strength Concentrate

| | |
|---|---|
| N—[(4,6-dimethoxypyrimidin-2-yl)aminocarbonyl]sulfamic acid, 2-(trifluoromethylthio)phenyl ester | 99% |
| silica aerogel | 0.5% |
| synthetic amorphous silica | 0.5% |

The ingredients are blended and ground in a hammer-mill to produce a material substantially all passing a U.S. Ser. No. 50 screen (0.3 mm opening). The concentrate may be formulated further if necessary.

EXAMPLE 22

Wettable Powder

| | |
|---|---|
| N—[(4,6-dimethoxypyrimidin-2-yl)aminocarbonyl]sulfamic acid, 2-(trifluoromethylthio)phenyl ester | 90% |
| dioctyl sodium sulfosuccinate | 0.1% |
| synthetic fine silica | 9.9% |

The ingredients are blended and ground in a hammer-mill to produce particles substantially all below 100 microns. The material is sifted through a U.S. Ser. No. 50 screen and then packaged.

EXAMPLE 23

Wettable Powder

| | |
|---|---|
| N—[(4,6-dimethoxypyrimidin-2-yl)aminocarbonyl]sulfamic acid, 2-(difluoromethylthio)phenyl ester | 40% |
| sodium ligninsulfonate | 20% |
| montmorillonite clay | 40% |

The ingredients are thoroughly blended, coarsely hammer-milled and then air-milled to produce particles substantially all below 10 microns in size. The material is reblended and then packaged.

EXAMPLE 24

Oil Suspension

| | |
|---|---|
| N—[(4,6-dimethoxypyrimidin-2-yl)aminocarbonyl]sulfamic acid, 2-(trifluoromethylthio)phenyl ester | 35% |
| blend of polyalcohol carboxylic esters and oil-soluble petroleum sulfonates | 6% |
| xylene | 59% |

The ingredients are combined and ground together in a sand mill to produce particles substantially all below 5 microns. The product can be used directly, extended with oils, or emulsified in water.

EXAMPLE 25

Dust

| | |
|---|---|
| N—[(4,6-dimethoxypyrimidin-2-yl)aminocarbonyl]sulfamic acid, 2-(trifluoromethylthio)phenyl ester | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

Utility

Test results indicate that the compounds of the present invention are active herbicides. They should have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, some of the subject compounds should be useful for the selective weed control in rice.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.125 to 10 kg/ha, the lower rates being suggested for use on lighter soils and/or those having a low organic matter content, for selective weed control or for situations where only short-term persistence is required.

The compounds of the invention can be used in combination with any other commercial herbicide, examples of which are those of the triazine, triazole, uracil, urea, amide, diphenyl ether, carbamate and bipyridylium types. They may also be used in combination with mefluidide.

The herbicidal properties of the subject compounds were discovered in a number of greenhouse tests. The test procedures and results follow.

Compounds
Compound 1
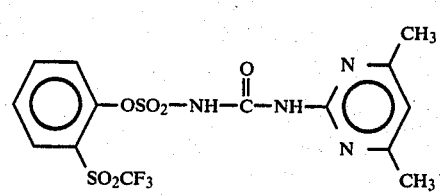
Compound 2
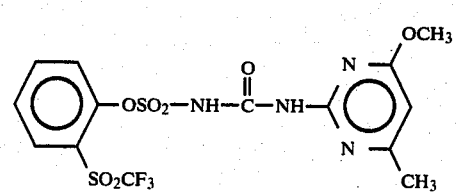
Compound 3
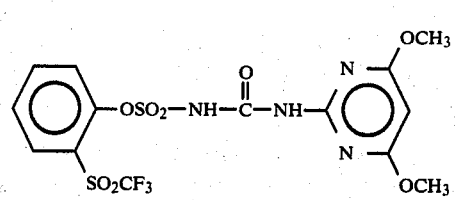
Compound 4
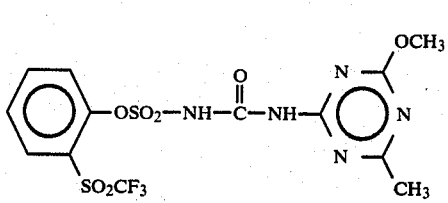
Compound 5
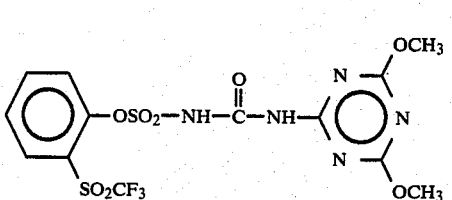
Compound 6
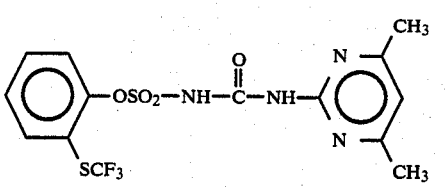
Compound 7
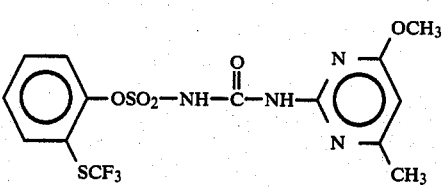
Compound 8
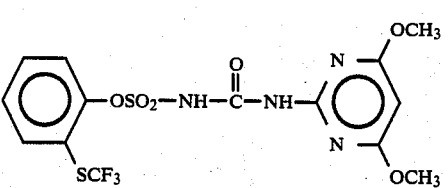
-continued
Compounds
Compound 9
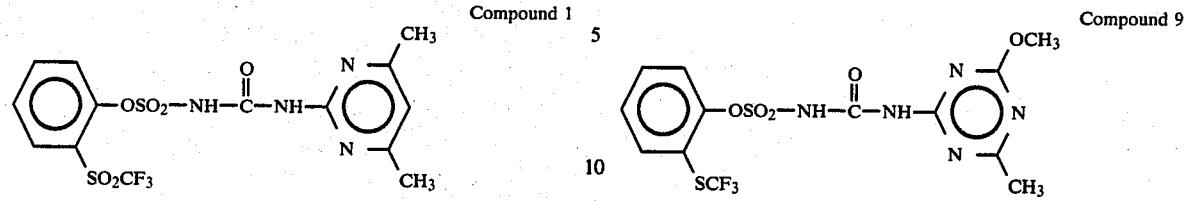
Compound 10
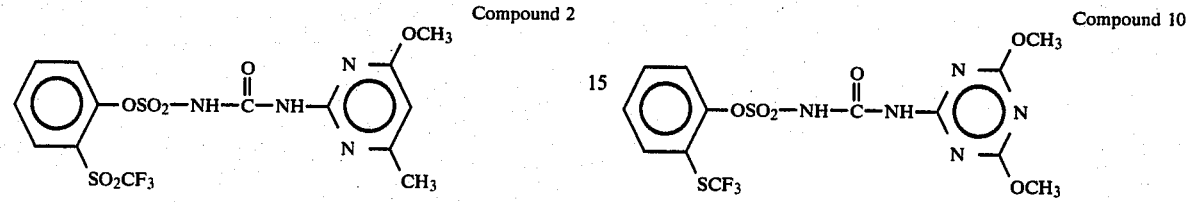
Compound 11
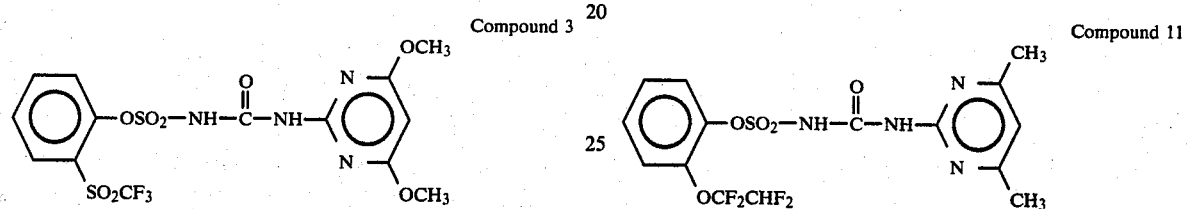
Compound 12
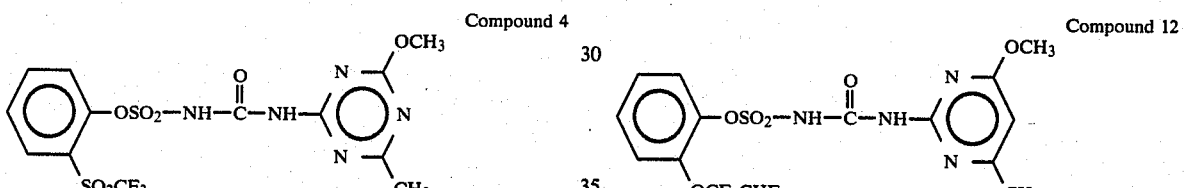
Compound 13
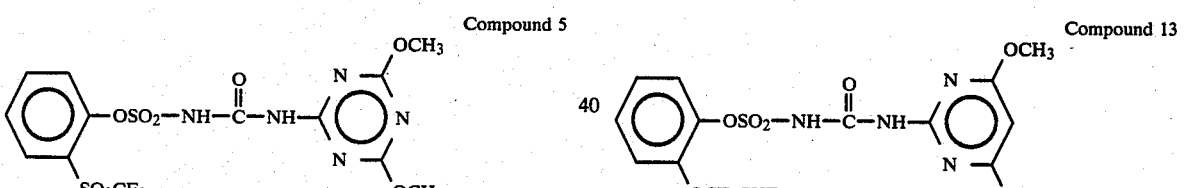
Compound 14
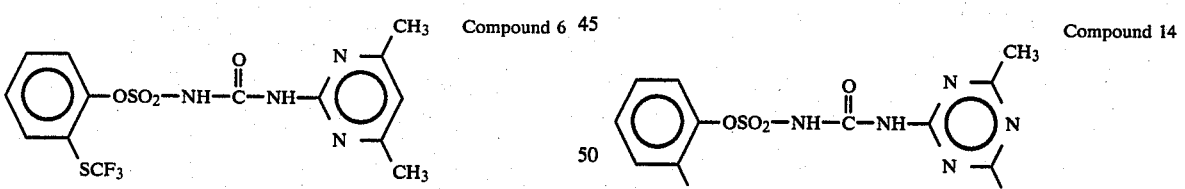
Compound 15
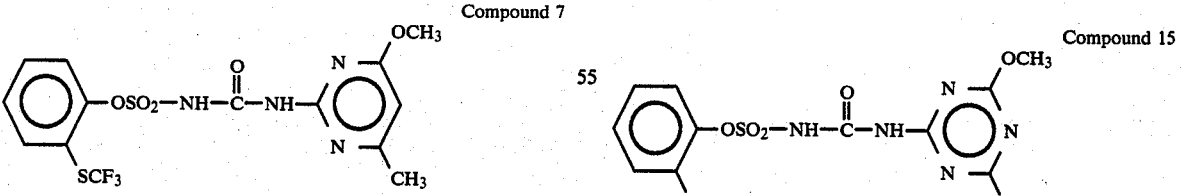
Compound 16
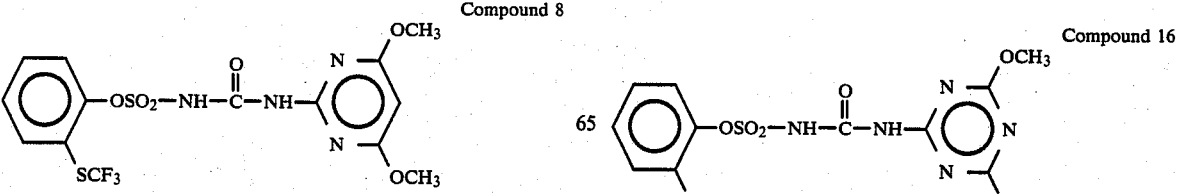

-continued
Compounds
Compound 17
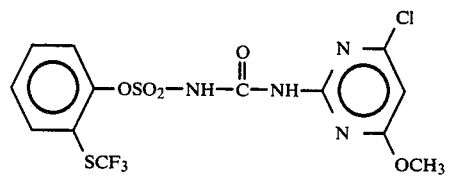
Compound 18
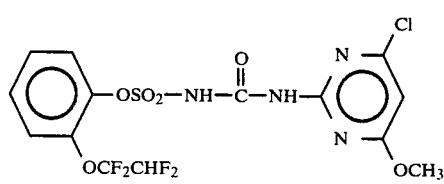
Compound 19
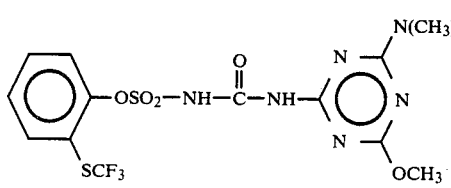
Compound 20
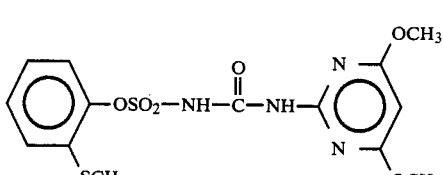
Compound 21
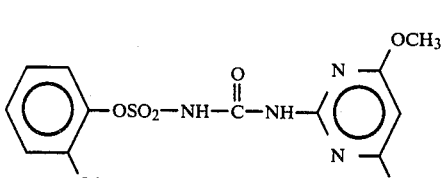
Compound 22
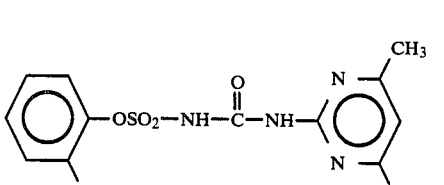
Compound 23
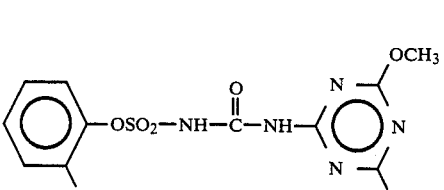
-continued
Compounds
Compound 24
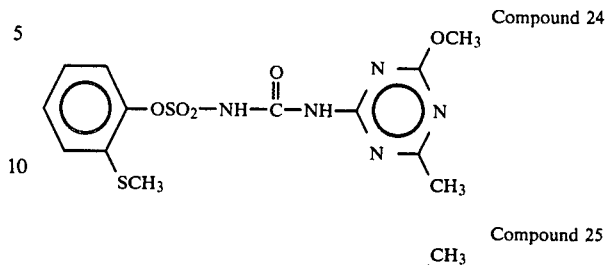
Compound 25
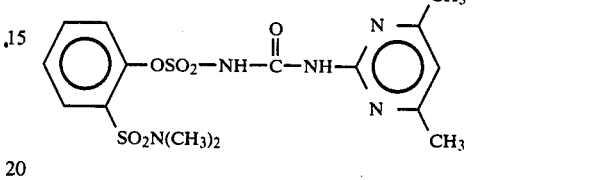
Compound 26
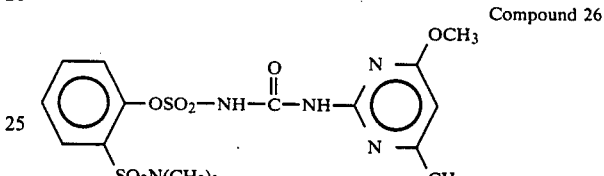
Compound 27
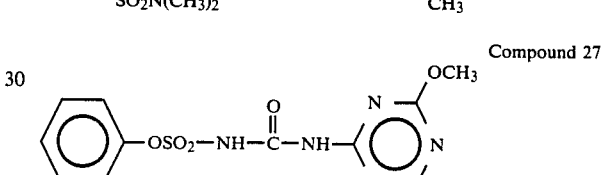
Compound 28
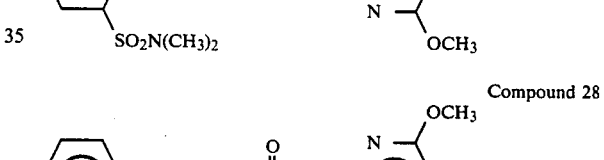
Compound 29
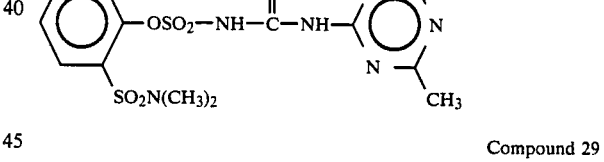
Compound 30
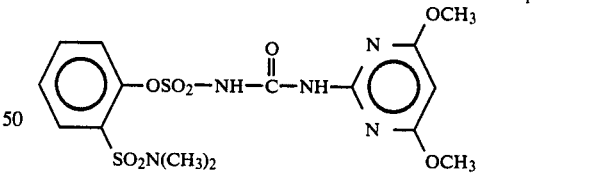
Compound 31
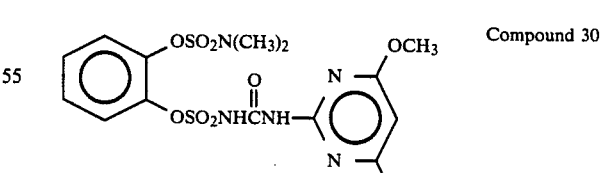
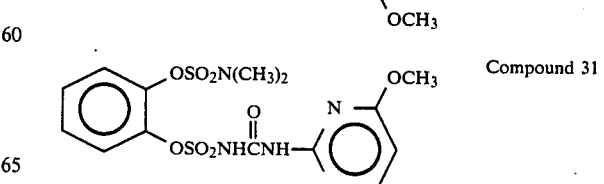

-continued
Compounds

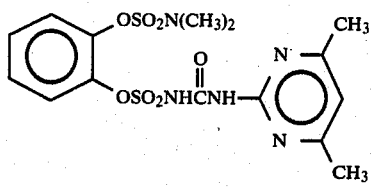 Compound 32

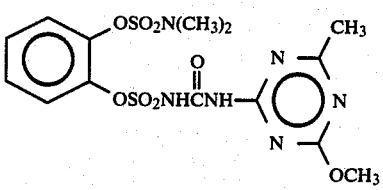 Compound 33

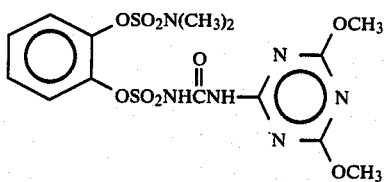 Compound 34

TEST A

Seeds of crabgrass (Digitaria spp.), barnyardgrass (Echinochloa crusgalli), wild oats (Avena fatua), sicklepod (Cassia obtusifolia), morningglory (Ipomoea spp.), cocklebur (Xanthium pensylvanicum), sorghum, corn, soybean, sugar beet, rice, wheat, and purple nutsedge )Cyperus rotundus) tubers were planted and treated preemergence with the test chemicals dissolved in a nonphytotoxic solvent. At the same time, these crop and weed species, along with cotton and bush bean, were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
E=emergence inhibition;
G=growth retardation;
H=formative effect; and
6Y=abscised buds or flowers.

The herbicidal and plant-growth-regulatory activity may be seen in the following Table A.

TABLE A
POST-EMERGENCE

| | Cmpd. 1 | Cmpd. 2 | Cmpd. 3 | Cmpd. 4 | Cmpd. 5 | Cmpd. 6 | Cmpd. 7 | Cmpd. 8 | Cmpd. 9 | Cmpd. 10 | Compound 11 | | Compound 12 | |
|---|---|---|---|---|---|---|---|---|---|---|---|---|---|---|
| | 0.05 | 0.05 | 0.05 | 0.05 | 0.05 | 0.05 | 0.05 | 0.05 | 0.05 | 0.05 | 2.0 | 0.05 | 2.0 | 0.05 |
| Bush bean | 0 | 0 | 7C,9G,6Y | 3C,2H,6Y | 2C,4H | 2C,3G | 2C,3G | 2C,5G,6Y | 2C,4G | 2C | 0 | 1C,4G | 4C,9G,6Y | 4C |
| Cotton | 1C | 0 | 3C,5H | 2C | 2C | 3C | 1C | 3C,5H | 2C | 3C | 0 | 0 | 3C,6H | 3C |
| Morningglory | 0 | 1C | 6C,9G | 1C | 2C,2H | 6C,9G | 2C | 6C,9G | 4C,8H | 9C | 2C | 0 | 5C,9G | 5C |
| Cocklebur | 2H | 1C,6G | 9C | 2C,6H | 2C,5H | 6C,9G | 2C,9G | 6C,9G | 5C,9G | 4H | 3C,9H | 0 | 9C | 1C |
| Sicklepod | 0 | 0 | 2C,4H | 1C | 2C,2H | 1C,3G | 0 | 3C,4G | 2C,3G | 1C,2H | 1C | 0 | 3C,4H | 4H |
| Nutsedge | 0 | 0 | 2C,9G | 0 | 0 | 2G | 0 | 5G | 0 | 0 | 0 | 0 | 3C,9G | 0 |
| Crabgrass | 0 | 0 | 0 | 0 | 0 | 2G | 0 | 2G | 0 | 0 | 0 | 0 | 3G | 0 |
| Barnyardgrass | 0 | 0 | 0 | 0 | 0 | 2G | 0 | 1H | 0 | 0 | 0 | 0 | 4H | 0 |
| Wild Oats | 0 | 0 | 0 | 0 | 0 | 0 | 0 | 0 | 0 | 0 | 0 | 0 | 0 | 0 |
| Wheat | 0 | 0 | 0 | 1H | 0 | 1H | 1H | 1H | 0 | 0 | 0 | 0 | 0 | 0 |
| Corn | 0 | 2G | 5C,9G | 0 | 2H | 3C,7G | 3C,7G | 5C,9G | 3C,9H | 2G | 0 | 0 | 2C,6G | 1C |
| Soybean | 0 | 0 | 0 | 0 | 1H,2G | 9C | 9C | 9C | 2C,4G | 2C,7G | 1C | 0 | 0 | 4G |
| Rice | 0 | 0 | 0 | 0 | 1C | 2C,3G | 2C,3G | 1C | 2C,4G | 2C,4H | 0 | 0 | 2C,3G | 0 |
| Sorghum | 0 | 0 | 0 | 2C | 3C | 5C,8G | 2C,8G | 2C,8G | 2C,3H | 2C,3G | 0 | 0 | 9C | 0 |
| Sugar beet | 3G | 3C,8G | 0 | 2C,7G | 3C,7G | | | | 3C,8H | 5C,8G | | | | |

| | Compound 13 | | Compound 14 | | Compound 15 | | Compound 16 | | Compound 17 | | | Compound 20 | | |
|---|---|---|---|---|---|---|---|---|---|---|---|---|---|---|
| | 2.0 | 0.05 | 2.0 | 0.05 | 2.0 | 0.05 | 2.0 | 0.05 | 2.0 | 0.05 | | 400 | 2000 | |
| Bush bean | 3C,8G,6Y | 2C,8G,6Y | — | 3G | 3C,6G,6Y | 3C,3H | 2C,2H | 2C | 2C | — | | 5C,9G | 5C,9G | |
| Cotton | 3C,9G | 4C | 0 | 0 | 3C,3H | 0 | 4C | 1C | 2C | 4C,8G | | 4C,8G | 5C,9G | |
| Morningglory | 5C,9G | 4C,5G | 10C | 2C | 5C,9G | 0 | 4C,9G | 2C,2H | 2C | 4C,8G | | 10C | 9C | |
| Cocklebur | 9C | 2C,9G | 8C | 0 | 5C,9G | 0 | 5C,9G | 0 | 1C,5G | 10C | | 5C,9G | 9C | |
| Sicklepod | 3C,8H | 2C | 4C,9G | 4C,9G | 4C,5H | 0 | 4C | 0 | 1C | 2C,7G | | 2C,7G | 6C,9G | |
| Nutsedge | 9C | 2C,5G | 1C | 2C | 2C,8G | 0 | 2C,8G | 0 | 0 | 4G | | 6C,9G | 4G | |
| Crabgrass | 2C,5G | 0 | 0 | 0 | 1C | 0 | 1C | 0 | 0 | 3C,7H | | 3C,6G | 3G | |
| Barnyardgrass | 2C,4G | 0 | 0 | 0 | 2C,4H | 0 | 3C,5H | 0 | 0 | 3C,7H | | 3C,9H | 4G | |
| Wild Oats | 0 | 0 | 0 | 0 | 0 | 0 | 0 | 0 | 0 | 1C | | 1C | 0 | |
| Wheat | 1C,3G | 0 | 0 | 0 | 1C,4H | 0 | 1C,5G | 1C,1H | 1H | 2G | | 1C | 0 | |
| Corn | 9C | 1C,3H | 1C | 1H | 3C,9H | 0 | 3C,6H | 0 | 1H | 2C,8H | | 2C,8H | 1H | |
| Soybean | 1C | 0 | 0 | 0 | 2C,5H | 0 | 5G | 0 | 0 | 4C,8G | | 5C,9G | 2C,2H | |
| Rice | 3G | 1C | 0 | 0 | 2C,8H | 0 | 2C,7G | 0 | 0 | 2G | | 1C,4G | 0 | |
| Sorghum | 9C | 2G | 3C,5H | 2C | 2C,8H | 3G | 3C,7H | 1C | 0 | 3C,9H | | 4C,9H | 1C,3G | |
| Sugar beet | | | 0 | 2C,6H | 9C | | | 2C,5G | | 5C,9G | | 5C,9G | 1C,2H | |

| | Cmpd. 24 | Cmpd. 25 | Cmpd. 26 | Cmpd. 27 | Cmpd. 28 | Compound 29 | | Compound 30 | | Cmpd. 31 | Cmpd. 32 | Cmpd. 33 | Cmpd. 34 |
|---|---|---|---|---|---|---|---|---|---|---|---|---|---|
| | 400 | 400 | 400 | 400 | 400 | 400 | 50 | 400 | 50 | 0.40 | 0.40 | 0.40 | 0.40 |
| Bush bean | — | — | — | — | — | 5C,9G,6Y | 6Y,4C,9G | — | 3C,5G | 5C,9G | 2C | 4C,6G | 4C,8G |
| Cotton | 0 | 1C | 10C | 0 | 2C,2H | 4C,9G | 4C,8G | 4C,8G | 9C | 10C | 3C,8G | 5C,9G | 4C,8G |
| Morningglory | 5C,9G | 2C | 8C | 1C | 3C,5H | 9C | 9C | 10C | 9C | 9C | 3C,8H | 4C,9H | 4C,9H |
| Cocklebur | 0 | 3C,8H | 4C,9G | 2C | 3C,5H | 6C,9G | 4C,6G | 9C | 3C,6G | 3C,6G | | 1C | |
| Sicklepod | | 2C | 2C,2H | 0 | 3C,8G | | | | 1C,4G | 2C | 3G | 0 | 1C |
| Cassia | | | | | | | | | | | | | |
| Nutsedge | 0 | 0 | 0 | 0 | 0 | 8G | 2C,9G | 5C,9G,6Y | 3C,7G | 2C | 0 | 0 | 0 |
| Crabgrass | 0 | 2C | 2C | 0 | 2C | 2C,8G | 7G | 9C | 0 | 0 | 0 | 0 | 0 |
| Barnyardgrass | 1C | 2C | 2C,5G | 0 | 2C | 3C,9H | 2C,8H | 2G | 2G | 0 | | | |

TABLE A-continued

| | Cmpd. 1 | Cmpd. 2 | Cmpd. 3 | Cmpd. 4 | Cmpd. 5 | Cmpd. 6 | Cmpd. 7 | Cmpd. 8 | Cmpd. 9 | Cmpd. 10 | Compound 11 | | Compound 12 | |
|---|---|---|---|---|---|---|---|---|---|---|---|---|---|---|
| | 0.05 | 0.05 | 0.05 | 0.05 | 0.05 | 0.05 | 0.05 | 0.05 | 0.05 | 0.05 | 0.05 | 2.0 | 0.05 | |
| Wild Oats | 0 | 0 | 0 | 0 | 0 | 1H | 0 | 0 | 0 | 0 | 0 | 0 | 0 | |
| Wheat | 0 | 0 | 1C | 0 | 0 | 1H | 0 | 0 | 0 | 0 | 0 | 0 | 0 | |
| Corn | 1H | 1C | 2G | 0 | 0 | 2C,9H | 0 | 0 | 0 | 3C,7H | 0 | 5H | 0 | |
| Soybean | 2H | 0 | 2C,9G | 0 | 2C,2H | 4C,9G | 2C,4G | 2C,6G | 3C,5H | 4C,8H | 2H | 0 | 3C,9G | |
| Rice | 0 | 0 | 2C,2G | 0 | 3C,4G | 3C,5G | 2C,7G | 3C,9G | 2C,9G | 2C | 0 | 0 | | |
| Sorghum | 2G | 1C | 2C,8H | 0 | 3C,8H | 2C,9H | 9C | 2C,7H | 2C,9H | 2C,6G | 0 | 2C,8H | 2C,8H | |
| Sugar beet | 2C,2H | 2C,3H | 4C,9G | 2C,3G | 3C,9G | 5C,9G | 9C | 9C | 5C,9G | 5C,8G | 2C | 4C,8H | 4C,7G | |

PRE-EMERGENCE

| | Compound 13 | | Cmpd. 14 | | Compound 15 | | Cmpd. 16 | | Cmpd. 17 | | Compound 20 | | Cmpd. 21 | Cmpd. 22 | Cmpd. 23 | |
|---|---|---|---|---|---|---|---|---|---|---|---|---|---|---|---|---|
| | 0.05 | 2.0 | 0.05 | 400 | 2.0 | 0.05 | 2.0 | 0.05 | 0.05 | 2000 | 400 | 2000 | 400 | 400 | 400 | 2000 |
| Morningglory | 7G | 9G | 0 | 2C | 9G | 2C | 9G | 2C | 9G | 9H | 0 | 8G | 8H |
| Cocklebur | 2H | 9H | 0 | 0 | 9H | 0 | 9H | — | 3H | 9H | 8H | 9H | 9G | 9G |
| Sicklepod | 0 | 8G | 0 | 0 | 3C | 0 | 4C,4H | 0 | 0 | 9G | 9G | 9G | 9G | 9G |
| Nutsedge | 0 | 9G | 0 | 0 | 5G | 0 | 5G | 0 | 0 | 10E | 10E | 10E | 10E | 10E |
| Crabgrass | 0 | 0 | 0 | 0 | 2G | 0 | 2G | 0 | 1C | 2C,5G | 2G | 2C,7G | 3G | 4G |
| Barnyardgrass | 0 | 2C,5H | 0 | 0 | 2C,6H | 1C | 8H | 1C | 0 | 3C,9H | 3G | 3C,8G | 2C | 2G |
| Wild Oats | 0 | 0 | 0 | 0 | 0 | 0 | 0 | 0 | 0 | 7G | 2G | 5G | 4G |
| Wheat | 0 | 2C,6G | 1C | 0 | 4G | 0 | 6G | 0 | 0 | 9G | 4G | 9G | 2C,8G |
| Corn | 1C | 6H | 1C,3G | 0 | 1C,9H | 2C,7G | 2C,7G | 0 | 0 | 3C,5H | 2C,9H | 3C,5H | 2C,5G | 4G | 8G |
| Soybean | 1C | 2C,4G | 0 | 0 | 2C,3H | 7G | 1C,1H | 0 | 0 | 9G | 3G | 9G | 0 | 5H | 1C | 2C,5H |
| Rice | 1C | 0 | 2C | 0 | 2C,6G | 2C,5G | 2C,6H | 0 | 0 | 3C,5H | 2G | 8G | 5G | 5G | 2G | 2C,7G |
| Sorghum | 0 | 2G | 2C,5G | 0 | 3C,9H | 2C | 2C,8H | 0 | 2C,5G | 5C,9H | 6G | 4C,9H | 6G | 6G | 2C,9H | 4C,9H |
| Sugar beet | 10E | 10E | 4H | 0 | 5C,9G | 5C,9G | 4C,9G | 2C,9G | 4H | 10E | 9G | 5C,9H | 9G | 8G | 5G | 8G |
| Cotton | | | | | | | | | | 2C,9G | | 2C,9G | 5G | | 8G | |

| | Cmpd. 24 | Cmpd. 25 | Cmpd. 26 | Cmpd. 27 | Cmpd. 28 | Compound 29 | Compound 30 | | Cmpd. 31 | Cmpd. 32 | Cmpd. 33 | Cmpd. 34 |
|---|---|---|---|---|---|---|---|---|---|---|---|---|
| | 400 | 400 | 400 | 400 | 400 | 400 | 50 | 400 | 0.40 | 0.40 | 0.40 | 0.40 |
| Morningglory | 0 | 0 | 9C | 0 | 2G | 9C | 9G | 9C | 9H | 7H | 9H | 9G |
| Cocklebur | — | 0 | 9H | 0 | 3H | 9H | 9H | 9H | 9H | 8H | 9H | 9H |
| Sicklepod | 0 | 0 | 3H,3C | 0 | | 9G | 0 | | 3C,7G | 0 | 3C | 3C |
| Cassia | | | | | | | | 4C,9G | 6G | 0 | 0 | 0 |
| Nutsedge | 9G | 0 | 0 | 0 | 10E | 10E | | 10E | | | | |

TABLE A-continued

| | | | | | | | | | | | | |
|---|---|---|---|---|---|---|---|---|---|---|---|---|
| Crabgrass | 2G | 0 | 0 | 2G | 2G | 2G | 1C | 1C | 1C | 0 | 0 | 0 |
| Barnyardgrass | 0 | 0 | 3C,8G | 1C | 2C,3G | 9H,4C | 4C,8H | 1C | 4C,6G | 0 | 3C,3H | 2C |
| Wild Oats | 2G | 0 | 2C | 0 | 1C | 2C,6G | 2C | 0 | 1C | 0 | 0 | 0 |
| Wheat | 0 | 0 | 2C | 0 | 3G | 2C,7G | 0 | 0 | 1C | 0 | 0 | 0 |
| Corn | 5G | 0 | 3C,8H | 2G | 3C,9H | 2C,9H | 9H | 7G | 3C,7G | 0 | 4C,9H | 2C,8H |
| Soybean | 0 | 0 | 2C,5H | 1C | 3C,6H | 3C,7H | 8H | 1C,1H | 3C,8H | 0 | 4G | 1C |
| Rice | 2G | 0 | 3C,8H | 1C | 3C,9H | 5C,9H | 5G | 0 | 6G | 0 | 3C,5G | 2G |
| Sorghum | 2C,9G | 0 | 4C,9G | 3C,7G | 4C,9H | 6C,9H | 2C,9H | 8G | 8H | 0 | 9C | 2C,9H |
| Sugar beet | 2C,8G | 0 | 5C,9G | 2C,5G | 4C,9G | 10E | 5C,9G | 5C,9G | 4C,9G | 4C,8H | 9C | 6C,9G |
| Cotton | 2G | 0 | 3C,6G | 0 | | | 9G | 5G | 2C,9G | 3G | 7G | 7G |

TEST B

Two plastic bulb pans were filled with fertilized and limed Woodstown sandy loam. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), morningglory (*Ipomoea hederacea*), sicklepod (*Cassia obtusifolia*), teaweed (*Sida spinosa*), velvetleaf (*Abutilon theophrasti*), and jimsonweed (*Datura stramonium*). A 12.5-cm diameter plastic pot was also filled with prepared soil and plated with rice and wheat. Another 12.5-cm pot was planted with sugar beets. The above four containers were treated pre-emergence with several test compounds within the scope of the invention.

Twenty-eight days after treatment, the plants were evaluated and visually rated for response to the chemical treatments with the rating system described previously for Test A. A summary of the data may be seen in Table B.

TABLE B

PRE-EMERGENCE ON WOODSTOWN SANDY LOAM

| Rate kg/ha | 0.03 | 0.12 | 0.03 | 0.12 |
|---|---|---|---|---|
| | Compound 2 | | Compound 6 | |
| Crabgrass | 0 | 0 | 0 | 2G |
| Barnyardgrass | 0 | 0 | 0 | 0 |
| Sorghum | 0 | 2G | 0 | 0 |
| Wild Oats | 0 | 0 | 0 | 0 |
| Johnsongrass | 0 | 0 | 0 | 0 |
| Dallisgrass | 0 | 0 | 0 | 0 |
| Giant foxtail | 0 | 0 | 0 | 0 |
| Ky. bluegrass | 0 | 0 | 0 | 0 |
| Cheatgrass | 0 | 0 | 0 | 0 |
| Sugar beets | 0 | 0 | 0 | 0 |
| Corn | 0 | 0 | 0 | 0 |
| Mustard | 5G | 8G | 6G | 9G |
| Cocklebur | 0 | 2G | 0 | 2G |
| Nutsedge | 0 | 0 | 0 | 3G |
| Cotton | 0 | 0 | 0 | 2G |
| Morningglory | 0 | 3G | 0 | 2G |
| Sicklepod | 0 | 0 | 0 | 0 |
| Teaweed | 0 | 0 | 0 | 6G |
| Velvetleaf | 0 | 2G | 0 | 0 |
| Jimsonweed | 0 | 2G | 0 | 0 |
| Soybean | 0 | 0 | 0 | 0 |
| Rice | 2G | 2G | 0 | 0 |
| Wheat | 0 | 0 | 0 | 0 |
| | Compound 7 | | Compound 8 | |
| Crabgrass | 0 | 0 | 0 | 0 |
| Barnyardgrass | 0 | 3G | 0 | 2G |
| Sorghum | 0 | 5G | 0 | 2G |
| Wild Oats | 0 | 2G | 0 | 2G |
| Johnsongrass | 0 | 4G | 0 | 4G |
| Dallisgrass | 0 | 0 | 0 | 0 |
| Giant foxtail | 0 | 2G | 0 | 0 |
| Ky. bluegrass | 0 | 0 | 0 | 0 |
| Cheatgrass | 0 | 0 | 2G | 3G |
| Sugar beets | 7G | 8G | 6G | 8G |
| Corn | 0 | 0 | 0 | 0 |
| Mustard | 9G | 10C | 10C | 10C |
| Cocklebur | 2G | 6G | 2G | 6G |
| Nutsedge | 2G | 8G | 6G | 8G |
| Cotton | 4G | 6G | 6G | 7G |
| Morningglory | 4G | 5G | 3G | 4G |
| Sicklepod | 0 | 3G | 3G | 4G |
| Teaweed | 2G | 6G | 5G | 7G |
| Velvetleaf | 2G | 8G | 4G | 7G |
| Jimsonweed | 6G | 9G | 6G | 9G |
| Soybean | 0 | 3G,2C | 2G | 4G |
| Rice | 0 | 0 | 2G | 3G |
| Wheat | 0 | 0 | 0 | 2G |
| | Compound 9 | | Compound 10 | |
| Crabgrass | 0 | 0 | 0 | 0 |
| Barnyardgrass | 0 | 2G | 0 | 2G |
| Sorghum | 0 | 7G | 0 | 0 |
| Wild Oats | 0 | 0 | 0 | 0 |
| Johnsongrass | 0 | 0 | 0 | 0 |
| Dallisgrass | 0 | 0 | 0 | 0 |
| Giant foxtail | 0 | 0 | 0 | 0 |
| Ky. bluegrass | 0 | 0 | 0 | 0 |
| Cheatgrass | 0 | 3G | 0 | 2G |
| Sugar beets | 3G | 9G | 0 | 7G |
| Corn | 0 | 0 | 0 | 0 |
| Mustard | 9G | 9G | 7G | 9G |
| Cocklebur | 3G | 7G | 0 | 0 |
| Nutsedge | 0 | 2G | 0 | 0 |
| Cotton | 0 | 2G | 0 | 0 |
| Morningglory | 2G | 3G | 0 | 3G |
| Sicklepod | 3G | 4G | 0 | 0 |
| Teaweed | 3G | 3G | 0 | 2G |
| Velvetleaf | 0 | 7G | 0 | 2G |
| Jimsonweed | 0 | 5G | 0 | 4G |
| Soybean | 0 | 2G,3C | 0 | 2G,2C |
| Rice | 0 | 0 | 0 | 4G |
| Wheat | 0 | 0 | 0 | 2G |

TEST C

Two ten-inch in diameter plastic pans lined with polyethylene liners were filled with prepared Woodstown sandy loam soil. One pan was planted with seeds of wheat (*Triticum aestivum*), barley (*Hordeum vulgare*), wild oats (*Avena fatua*), cheatgrass (*Bromus secalinus*), blackgrass (*Alopecurus myosuroides*), annual bluegrass (*Poa annua*), green foxtail (*Setaria viridis*), Italian ryegrass (*Lolium multiflorum*) and ripgut brome (*Bromus rigidus*). The other pan was planted with seeds of Russian thistle (*Salsola kali*), tansy mustard (*Descuraina pinnata*), cleavers (*Galium aparine*), tumble mustard (*Sisymbrium altissium*), kochia (*Kochia scoparia*), shepherd's purse (*Capsella bursa-pastoris*), *Matricaria inodora*, black nightshade (*Solanum nigrum*), yellow rocket (*Barbarea vulgaris*), rapeseed (*Brassica napus*), and wild buckwheat (*Polygonum convolvulus*). The above two pans were treated pre-emergence. At the same time, two pans in which the above plant species were growing were treated post-emergence. Plant height at the time of treatment ranged from 1–15 cm depending on plant species.

The test compound was diluted with a non-phytotoxic solvent and sprayed over the top of the pans. An untreated control and a solvent-alone control were included for comparison. The treatments were maintained in the greenhouse for 19–21 days at which time the treatments were compared to the controls and the effects visually rated. The recorded data may be seen in Table C.

TABLE C

| | Compound 1 | | | |
|---|---|---|---|---|
| | Pre-Emergence | | Post-Emergence | |
| Rate kg/ha | 0.015 | 0.06 | 0.015 | 0.06 |
| wheat | 0 | 0 | 0 | 2G |

TABLE C-continued

| | Compound 1 | | | |
|---|---|---|---|---|
| | Pre-Emergence | | Post-Emergence | |
| Rate kg/ha | 0.015 | 0.06 | 0.015 | 0.06 |
| barley | 0 | 0 | 0 | 3G |
| wild oats | 0 | 0 | 0 | 2G |
| downy brome | — | — | — | — |
| cheatgrass | 0 | 0 | 0 | 4G |
| blackgrass | 3G | 0 | 0 | 3G |
| annual bluegrass | 2G | 0 | 0 | 3G |
| green foxtail | 3G | 0 | 0 | 0 |
| quackgrass | — | — | — | — |
| Italian ryegrass | 3G | 2G | 0 | 2G |
| ripgut brome | — | — | — | — |
| Russian thistle | 0 | 0 | 0 | 0 |
| tansy mustard | — | — | 5G | 7G |
| smartweed | — | — | 0 | 3G |
| tumble mustard | 8G | 9G | 0 | 10C |
| kochia | 0 | 0 | 0 | 0 |
| shepherd's purse | 8G | 10C | 6G | 10C |
| *Matricaria inodora* | 9G | 9C | 8G | 7C,9G |
| black nightshade | 3G | 5G | 3G | 4G |
| yellow rocket | 7G | 8G | 3G | 7G |
| wild mustard | 6G | 9G | 6G | 7G |
| wild buckwheat | 0 | 3G | 2G | 5G |
| *Veronica persica* | 2G | 4G | | |

TEST D 12-cm Diameter waxed paper cups were partially filled with Woodstown sandy loam. About 750 ml of water was added to each cup to bring the water level to a point 3 cm above the soil surface. Japonica rice seed was added to one set of pots, the seeds coming to rest on the soil surface (direct seeded rice). Japonica rice seedlings in the 2.5 leaf stage were transplanted into a second set of pots. Five days after seeding and transplanting Compound No. 8, dissolved in a small volume of acetone, was injected into the water of the simulated rice paddy. The rates of application and the crop response ratings made 10 days after treatment are shown in Table D.

TABLE D

| Compound No. | Rate (g/ha) | Transpl. Rice | Direct-seeded Rice |
|---|---|---|---|
| 8 | 0.25 | 0 | 0 |
| | 1 | 0 | 30 |
| | 4 | 0 | 60 |
| | 16 | 0 | 50 |
| | 62 | 0 | 50 |
| | 250 | 0 | 50 |
| | 1000 | 0 | 80 |

It will be seen that transplanted rice, in particular, is highly tolerant of Compound No. 8.

TEST E 16-cm Diameter glazed clay Waguer pots, equipped with a stoppered drain opening near the bottom of the side wall, were partially filled with Woodstown sandy loam. About 1500 ml of water was added to each pot to bring the water level to a point 3 cm above the soil surface. Direct-seeded Japonica rice was "planted" and Japonica rice seedlings were transplanted as described in Test D. Also, a number of barnyardgrass (*Echinochloa orusgalli*) seeds were added to each pot. At the same time, seedlings or tubers of the following species were transplanted into the muddy soil, water plantain (*Alisma trivale*), Scirpus (*Scirpus mucranatus*), and Cyperus (*Cyperus difformis*). The weed species selected for this test are of economic importance in major rice-growing areas. The chemical treatments were applied as described in Test D, within hours after transplanting of 2 additional species: water chestnut (Eleocharis spp.) and arrowhead (*Sagittaria latifolia*). Shortly after treatment, the drain hole was opened to drop the water level by 2 cm. Water was then added to restore the water level to its original height. The following day, the draining and refilling process was repeated. The pots were then maintained in the greenhouse. Rates of application and plant response ratings made 21 days after treatment are summarized in Table E.

TABLE E

| | Compound No. 8 | |
|---|---|---|
| Rate (g/ha) | 30 | 125 |
| Transpl. Rice | 10 | 20 |
| Direct-seeded Rice | 50 | 70 |
| Echinochloa | 50 | 70 |
| Eleocharis | 100 | 100 |
| Sagittaria | 100 | 100 |
| Scirpus | 50 | 80 |
| Cyperus | 100 | 100 |
| Alisum | 90 | 100 |

The data indicate that Compound 8 has potential utility for selective weed control in rice.

TEST F

The test procedure of Test E was repeated utilizing a different range of treatment rates. In addition to the above-mentioned species, Monocharia (*Monocharia vaginalis*) seeds were added to each pot in the same manner as barnyardgrass seed. The plant response ratings, taken 21 days after treatment, are given in Table F. They confirm the selective properties observed in previous tests.

TABLE F

| | Compound No. 8 | | | | |
|---|---|---|---|---|---|
| Rate (g/ha) | 2 | 8 | 16 | 30 | 125 |
| Transpl. Rice | 0 | 0 | 0 | 0 | 20 |
| Direct-seeded Rice | 0 | 0 | 0 | 0 | 20 |
| Echinochloa | 0 | 0 | 25 | 50 | 70 |
| Eleocharis | 0 | 60 | 100 | 100 | 100 |
| Sagittaria | 0 | 0 | 50 | 85 | 100 |
| Scirpus | 0 | 0 | 0 | 50 | 80 |
| Cyperus | 0 | 50 | 75 | 75 | 100 |
| Alisum | 0 | 50 | 30 | 90 | 100 |
| Monocharia | 0 | 25 | 80 | — | — |

What is claimed is:

1. A compound of the formula:

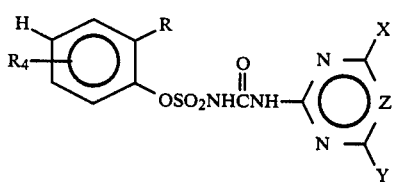

wherein
R is $QR_1$, $SO_2NR_2R_3$ or $OSO_2NR_2R_3$;
$R_1$ is $CH_2CH=CH_2$, $CF_3$, $CF_2H$ or $CF_2CF_2H$;
$R_2$ and $R_3$ are independently $C_1$–$C_3$ alkyl;
$R_4$ is H, $CH_3$, $OCH_3$, Cl, $NO_2$, F or $CF_3$;
Q is O, S, S(O) or $SO_2$;
X is $CH_3$ or $OCH_3$;
Y is $CH_3$, $OCH_3$, $C_2H_5$, $OC_2H_5$, $CH_2OCH_3$, $CH(OCH_3)_2$, Cl, Br or

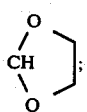

and
Z is CH;
and their agriculturally suitable salts provided that:
(1) the total number of carbon atoms of $R_2$ and $R_3$ is less than or equal to 4;
(2) when Y is Cl or Br, then X is $OCH_3$; and
(3) when Q is O, then $R_1$ is $CF_3$, $CF_2H$ or $CF_2CF_2H$.

2. Compounds of claim 1 where
R is $QR_1$ or $SO_2NR_2R_3$;
Q is O, S or $SO_2$;
$R_1$ is $C_1$–$C_3$ alkyl, $CH_2CH=CH_2$, $CF_3$ or $CF_2H$; and
$R_4$ is H.

3. Compounds of claim 2 where
$R_1$ is $CH_3$, $CF_3$ or $CF_2H$;
$R_2$ and $R_3$ are $CH_3$; and
Q is O or S.

4. The compound of claim 1 which is N-[(4,6-dimethoxypyrimidin-2-yl)aminocarbonyl]sulfamic acid, 2-(trifluoromethylthio)phenyl ester.

5. The compound of claim 1 which is N-[(4,6-dimethoxypyrimidin-2-yl)aminocarbonyl]sulfamic acid, 2-(trifluoromethylsulfonyl)phenyl ester.

6. A composition suitable for controlling the growth of undesired vegetation which comprises an effective amount of a compound of claim 1 and at least one of the following: surfactant, solid or liquid inert diluent.

7. A composition suitable for controlling the growth of undesired vegetation which comprises an effective amount of a compound of claim 2 and at least one of the following: surfactant, solid or liquid inert diluent.

8. A composition suitable for controlling the growth of undesired vegetation which comprises an effective amount of a compound of claim 3 and at least one of the following: surfactant, solid or liquid inert diluent.

9. A composition suitable for controlling the growth of undesired vegetation which comprises an effective amount of the compound of claim 4 and at least one of the following: surfactant, solid or liquid inert diluent.

10. A composition suitable for controlling the growth of undesired vegetation which comprises an effective amount of the compound of claim 5 and at least one of the following: surfactant, solid or liquid inert diluent.

11. A method for controlling the growth of undesired vegetation which comprises applying to the locus to be protected an effective amount of a compound of claim 1.

12. A method for controlling the growth of undesired vegetation which comprises applying to the locus to be protected an effective amount of a compound of claim 2.

13. A method for controlling the growth of undesired vegetation which comprises applying to the locus to be protected an effective amount of a compound of claim 3.

14. A method for controlling the growth of undesired vegetation which comprises applying to the locus to be protected an effective amount of the compound of claim 4.

15. A method for controlling the growth of undesired vegetation which comprises applying to the locus to be protected an effective amount of the compound of claim 5.

* * * * *